United States Patent [19]
Park et al.

[11] Patent Number: 5,947,708
[45] Date of Patent: Sep. 7, 1999

[54] AXIAL FLOW VALVE SYSTEM FOR LINEAR COMPRESSOR

[75] Inventors: Jung Sik Park; Hyung Kook Lee, both of Kyungki-Do, Rep. of Korea

[73] Assignee: LG Electronics Inc., Rep. of Korea

[21] Appl. No.: 08/817,135

[22] PCT Filed: Aug. 20, 1996

[86] PCT No.: PCT/KR96/00140

§ 371 Date: Apr. 9, 1997

§ 102(e) Date: Apr. 9, 1997

[87] PCT Pub. No.: WO97/07334

PCT Pub. Date: Feb. 27, 1997

[30] Foreign Application Priority Data

Aug. 21, 1995 [KR] Rep. of Korea ................ 95-25664
Aug. 21, 1995 [KR] Rep. of Korea ................ 95-25665

[51] Int. Cl.⁶ ........................ F04B 39/10; F16K 15/16
[52] U.S. Cl. .................... 417/552; 417/570; 137/856
[58] Field of Search ............................ 417/552, 570; 137/856, 855, 637, 597, 614.04, 614.05, 614.06, 614.13, 614.14

[56] References Cited

U.S. PATENT DOCUMENTS

| | | |
|---|---|---|
| 1,496,432 | 6/1924 | Robinson . |
| 1,682,736 | 9/1928 | Berry . |
| 1,764,655 | 6/1930 | Spreen . |
| 2,296,833 | 9/1942 | Trask ........................ 417/550 |
| 2,622,792 | 12/1952 | Ramclow ................. 417/550 |
| 3,123,095 | 3/1964 | Kohler ................... 137/516.23 |
| 4,542,768 | 9/1985 | Harris ........................ 137/856 |
| 4,834,632 | 5/1989 | Gatecliff et al. .......... 417/534 |
| 4,955,796 | 9/1990 | Terwilliger .............. 417/547 |
| 5,266,015 | 11/1993 | Gannaway ................ 417/550 |

FOREIGN PATENT DOCUMENTS 1503459  1/1971  Germany .

OTHER PUBLICATIONS

International Search Report–From PCT Application No. PCT/KR96/00140–Date of Internation Search Nov. 13, 1996.

Primary Examiner—Charles G. Freay
Assistant Examiner—Paul Ratcliffe
Attorney, Agent, or Firm—Ostrolenk, Faber, Gerb & Soffen, LLP

[57] ABSTRACT

An axial flow valve system for a linear compressor which is capable of enhancing the operation of the compressor by securely fixing an intake valve comprising an axial flow valve system to prevent an undesired axial movement of the intake valve, promptly carrying out an opening-closing operation and improving the reliability of the valve opening-closing operation.

10 Claims, 11 Drawing Sheets

AXIAL FLOW VALVE SYSTEM FOR LINEAR COMPRESSOR

TECHNICAL FIELD

The present invention relates to an axial flow valve system for a linear compressor, and in particular, to an improved axial flow valve system for a linear compressor which is capable of enhancing the operation of the compressor by securely fixing an intake valve comprising the axial flow valve system to prevent an undesired axial movement of the intake valve, promptly carrying out the opening-closing operation and improving the reliability of a valve opening-closing operation.

BACKGROUND ART

Recently, in order to overcome the deficiencies of a compressor employing a rotating crank shaft, there has been developed a linear type compressor for reciprocally moving a piston using a magnet and a coil instead of a crankshaft, whereby the number of components and the manufacturing cost can be reduced, resulting in an improvement in productivity. Simultaneously, the motor efficiency has been enhanced up to more than 90%, and the electrical consumption has been diminished.

In a typical linear compressor according to the conventional art, as shown in FIG. 1, a cylinder 2 is provided having a predetermined space from an inner bottom surface of an enclosed container 1.

Inside the cylinder, coil assemblies 3,3' are formed to be integral with the cylinder 2.

At a portion of the cylinder 2, a piston spring 4 is fixed, and a piston 5 is connected to an inner central portion of the piston spring 4, which connection enables the piston 5 to make a linear reciprocable movement within the cylinder 2.

A magnet 6 is affixed to an outer circumferential surface of the piston 5, and a plurality of mountain springs 7 are connected between the piston spring 4 and the enclosed container 1 to resiliently support the piston spring 4.

A valve assembly 8 is affixed on a central portion of one end of the cylinder 2, and an intake muffler 9 and an exhaust muffler 10 are affixed to respective sides of the valve assembly 8.

In the above-described linear compressor according to the conventional art, the coil assembly 3,3' affixed to the cylinder 2 and the magnet 6 affixed to the piston 5 carry out a function of a linear motor.

That is, by electromagnetic energy and a resilient force, the piston 5 repeatedly carries out a linear reciprocating movement inside the cylinder 2, and thereby draws a refrigerant through an intake valve comprising the valve assembly 8, and compresses the refrigerant in a compression chamber (C), and then discharges the compressed refrigerant through an exhaust valve.

Here, the intake muffler 9 and the exhaust muffler 10 respectively provided at an intake side and an exhaust side reduce noise in the refrigerant.

In the above-described conventional linear compressor, the opening-closing portions of the valves controlling the flow of the refrigerant are a basic factor in improving the efficiency of the compressor. Therefore, in order to enhance the efficiency of the compressor, there is known an axial flow valve system which has the same flow direction of the refrigerant as the movement direction of the piston.

In an inertia-mode(for opening and closing the intake valve using inertia) valve system employed in the conventional linear compressor, as shown in FIG. 2, a cylindrical groove 2a is provided in a portion of an inner circumferential surface of the cylinder 2A.

In addition, at a central front portion of the piston 5A, an intake valve 11 is affixed with a caulking by a piston pin 12. Here, the intake valve 11 is disposed to be moved to the left and right, and therefore can control the flow of the refrigerant in accordance with the movement direction of the piston 5A.

A head cover 13 is connected to one end of the cylinder 2A, and an exhaust valve 14 and a spring 15 are disposed inside the head cover 13. Therefore, when the pressure of the refrigerant gas compressed in the compression chamber (C) of the cylinder 2A exceeds the resilient force of the spring 15, the refrigerant pushes open the exhaust valve 14, and then is exhausted through the head cover 13.

Reference numeral 5b denotes a threaded hole for receiving the threaded pin 12, reference numeral 11a denotes a pin hole in the intake valve 11, and reference numeral 13a denotes a refrigerant exhaust pipe disposed in the head cover 13.

In the inertia-mode valve apparatus for the conventional linear compressor, in the intake cycle the refrigerant is sucked into the piston 5A through the refrigerant intake port 2b of the cylinder 2A and the piston groove 5a when the piston 5A is moved away from the exhaust valve 14 in the intake cycle, and since the intake valve 11 is opened by inertia, the refrigerant flows in between the intake valve 11 and the piston 5A and into the compression chamber (C).

Here, movement of the intake valve 11 beyond a predetermined distance is limited by the piston pin 12.

Then, as shown in FIG. 3, when the compression cycle is performed, the refrigerant in the compression chamber (C) is compressed and thereby the pressure on the exhaust valve 14 exceeds the force of the spring and the valve 14 is moved away from the piston 5A, resulting in the exhausting of the compressed refrigerant through the refrigerant exhaust pipe 13a of the head cover 13. Here, the intake valve 11 is closely contacted with the front surface of the cylinder 2A and therefore the minimum clearance volume is maintained.

After the above-described compression cycle, as shown in FIG. 4, as the piston 5A moves away from the exhaust valve 14, the intake valve 11 is distanced from the front surface of the piston 5A, and then the above-described intake cycle is repeated. Here, the exhaust valve 14 is returned to its initial condition by the restoring force of the spring 15.

FIGS. 5 through 8 shows a valve apparatus for a linear compressor according to the conventional art, and a first exhaust valve 14A and a second exhaust valve 14B, namely a closing member for the first exhaust valve, inside the head cover 13 are illustrated.

At a central portion of the first-exhaust valve 14A, as shown in FIG. 7, a refrigerant exhaust port 14a is formed, and as shown in FIG. 8, the second exhaust valve 14B is formed in a spiral shape for opening and closing the refrigerant exhaust port 14a of the exhaust valve 14A.

The same elements as in FIG. 2 are indicated by the same reference numerals.

In this other axial flow valve apparatus for a linear compressor according to the conventional art, after the refrigerant is sucked into the piston 5A through the refrigerant intake port 2b of the cylinder 2A and the cylinder groove 2a, and flows in between the piston 5A and the intake valve 11 to fill the compression chamber (C).

Here, since the intake valve 11 is fixed to the piston 5A by the piston pin, the valve 11 may not move beyond a predetermined distance.

Then, when the piston 5A is moved in the direction of the first exhaust valve 14A and the compression cycle is performed, the compressed refrigerant flows into the exhaust port 14a of the first exhaust valve 14A.

Here, as shown in FIGS. 7 and 8, when the piston pin 12 is inserted in the exhaust port 14a of the first exhaust valve 14A during the compression stroke, the central portion of the second exhaust valve 14B is pushed open and the compressed refrigerant is exhausted through the refrigerant exhaust pipe 13a of the head cover 13.

That is, the second exhaust valve 14B is opened and closed on its own, resulting in a prompt opening and closing of the valve 14B.

Here, when the front end of the piston 5A contacts with the first exhaust valve 14A, the force of the spring 15 is applied to the first exhaust valve 14A and the second exhaust valve 14B, resulting in the stable operation of the exhaust valves.

But, in the axial flow valve apparatus for the linear compressor according to the conventional art, in the case of the former apparatus, since the exhaust valve 14 is resiliently supported by the spring 15, when the exhausting of the compressed refrigerant is performed, the opening and closing of the exhaust valve proceeds slowly, and the intake valve 11 may stick to the front surface of the piston 5A due to the pressure of oil used for the lubrication of the piston 5A, and friction may be produced between the intake valve 11 and the piston pin 12, or the repeated movement of the intake valve 11 may disadvantageously cause the diameter of the pin hole 11a of the intake valve 11 integral with the piston pin 12 to become gradually larger. Consequently, the operation of the intake valve 11 may become unstable, and the efficiency of the linear compressor may become lowered.

And, in the case of the latter conventional linear compressor, the double exhaust valve construction using the first exhaust valve 14A and the second exhaust valve 14B is employed, and as a result, a prompt opening and closing of the exhaust valve is preferably carried out. However, since the intake valve is moved by the axial flow, defects caused by the oil in the former apparatus cannot be overcome, and since the second exhaust valve 14B is in the shape of a resilient thin film and much displacement occurs therein during the exhaust of the refrigerant, if the valve 14B is used for an long time, the reliability of the valve operation can become lowered.

DISCLOSURE OF THE INVENTION

The prime object of the present invention is to provide an improved axial flow valve system for a linear compressor which is capable of achieving a prompter opening and closing operation and enhancing the reliability of the opening and closing operation of a valve.

Another object of the present invention is to provide an improved axial flow valve system for a linear compressor which is capable of enhancing the efficiency of the compressor by preventing the intake valve from sticking to the front surface of the piston due to the oil supplied for lubrication of the piston and for preventing friction between the intake valve and a piston pin.

Still another object of the present invention is to provide an improved axial flow valve system for a linear compressor which is capable of enhancing the efficiency of the compressor by securably affixing an intake valve on the front surface of the piston.

To achieve the above object, there is provided an improved axial flow valve system for a linear compressor which includes an intake valve closely fixed without rocking on a central portion of a front end of a piston disposed inside a cylinder by a piston pin for passing a refrigerant, first and second exhaust valves provided in an inner bore of a head cover fixed to one end of the cylinder, a resilient member disposed at one side of the inner bore of the head cover for resiliently supporting the first and second exhaust valves, and a stopper provided between the second exhaust valve and the resilient member for preventing the second exhaust valve from being pushed rearwardly.

To achieve the above object, there is provided an improved axial flow valve system for a linear compressor which includes a piston disposed inside a cylinder and having a recessed front end, an intervalve closely combined at a central portion of the front end of the piston, an intake valve contacted with the intervalve and fixed to the piston without rocking to pass a refrigerant, having a fixing hole at a center thereof for being fastened by a piston pin, and at its peripheral portion having a resilient for opening and closing the piston port disposed in a front portion of the piston, a resilient member disposed at one side of an inner bore a head cover for resiliently supporting the first exhaust valve, the second exhaust valve and the stopper, and a stopper provided between the second exhaust valve and the resilient member for preventing the second exhaust valve from being pushed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

MODES FOR CARRYING OUT THE INVENTION

Referring to the accompanying drawings, an axial flow valve system for a linear compressor according to the present invention will now be described in detail.

Figure 1:
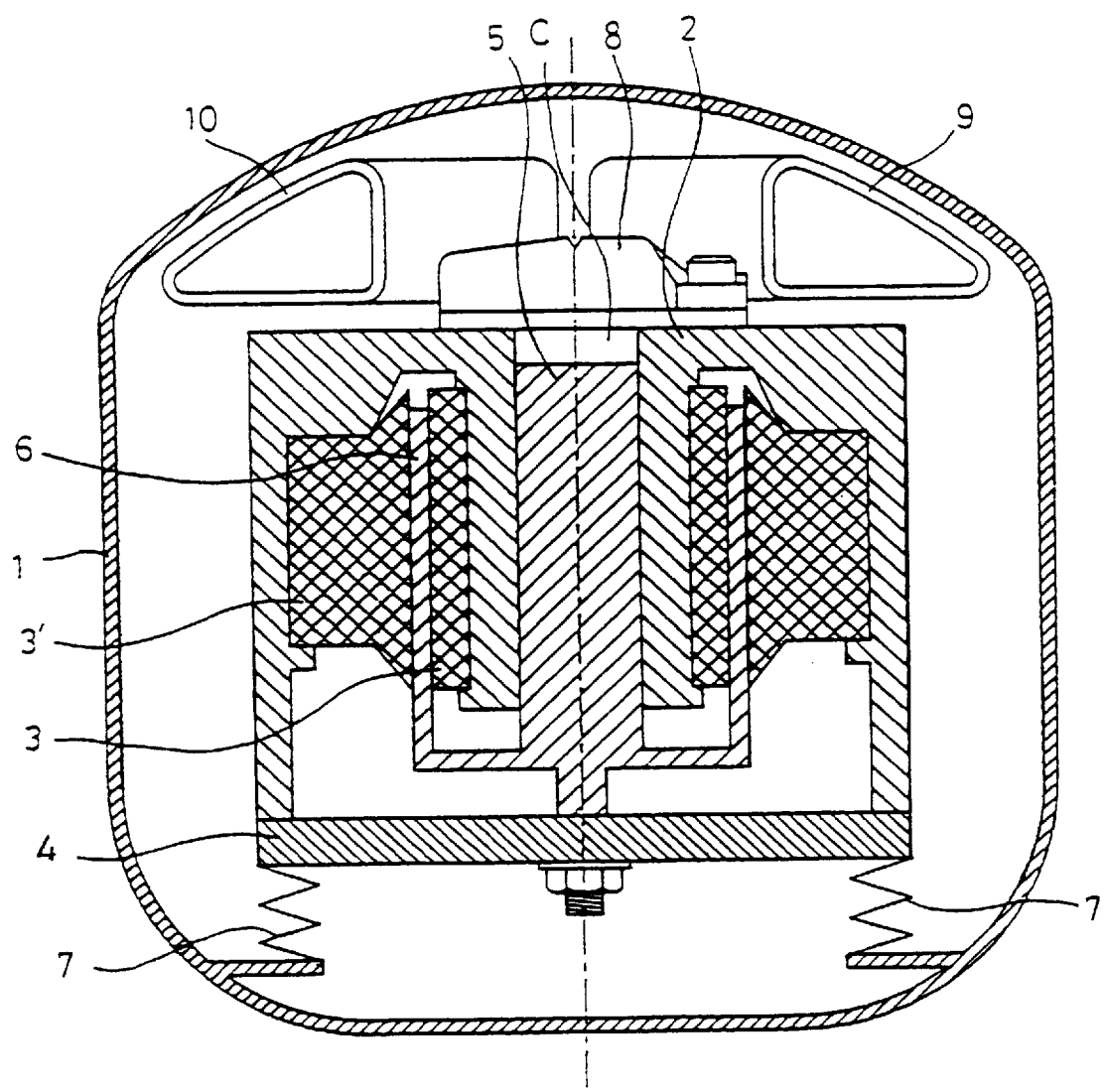
FIG. 1 is a cross-sectional view showing the construction of a linear compressor according to the conventional art.
Figure 2:
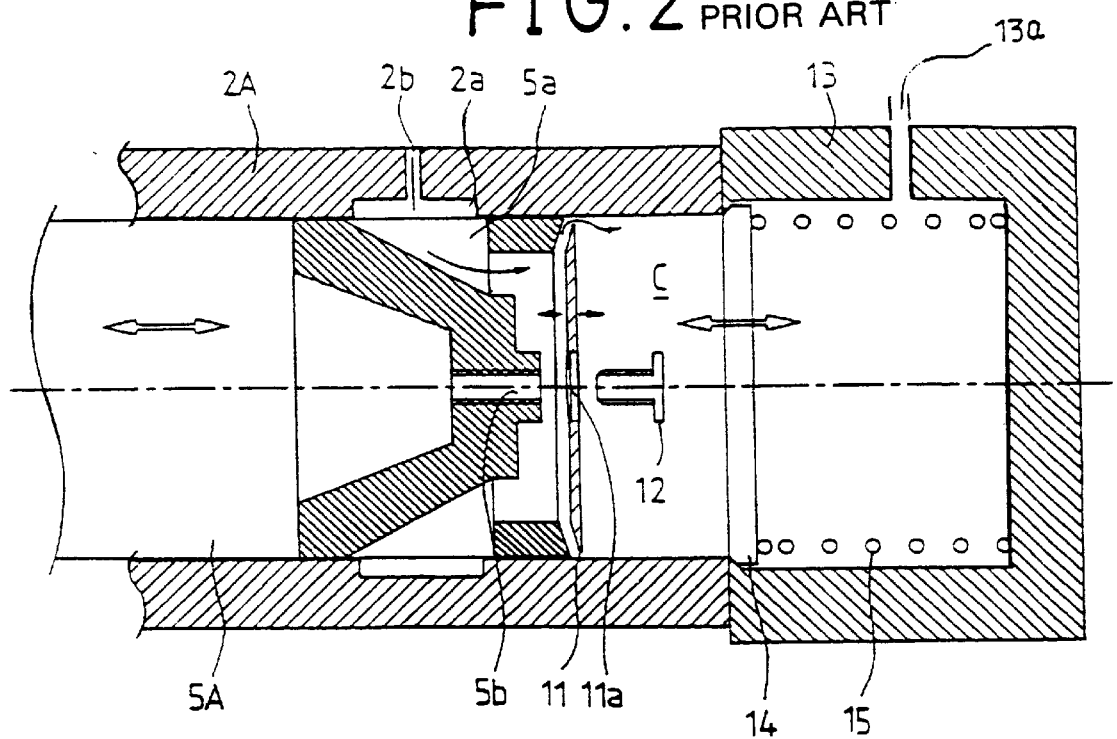
FIG. 2 is a cross-sectional view showing a part of an axial flow valve system for a linear compressor according to the conventional art.
Figure 3:
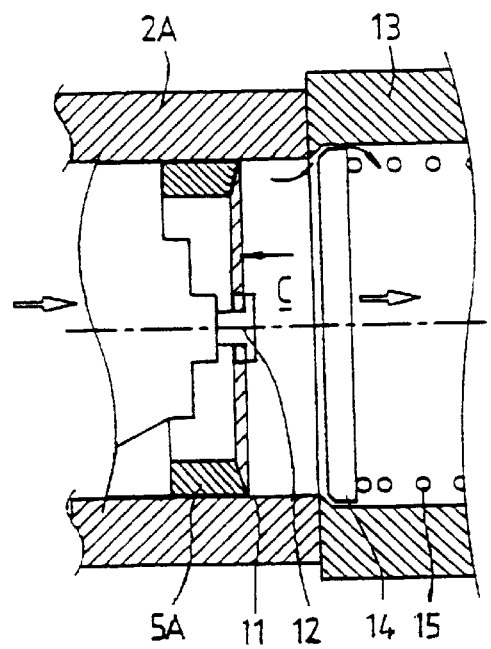
FIG. 3 is a cross-sectional view showing an axial flow valve system for a linear compressor during the compression cycle according to the conventional art.
Figure 4:
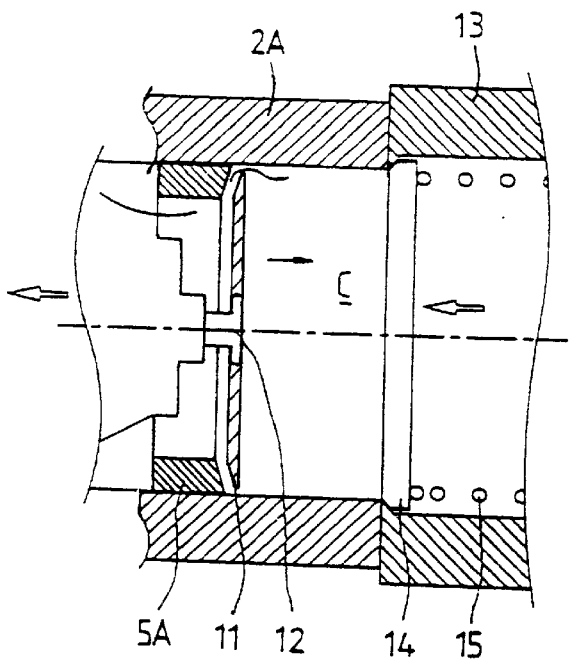
FIG. 4 is a cross-sectional view showing an axial flow valve system for a linear compressor during the intake cycle according to the conventional art.
Figure 5:
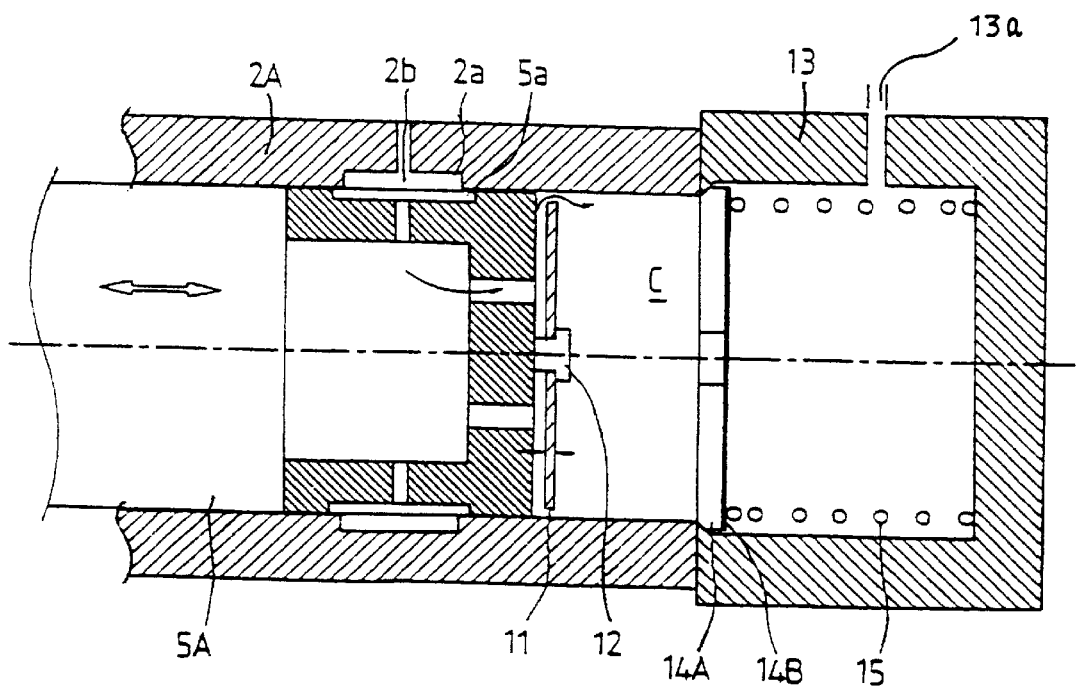
FIG. 5 is a cross-sectional view showing the construction of another axial flow valve system for a linear compressor according to the conventional art.
Figure 6:
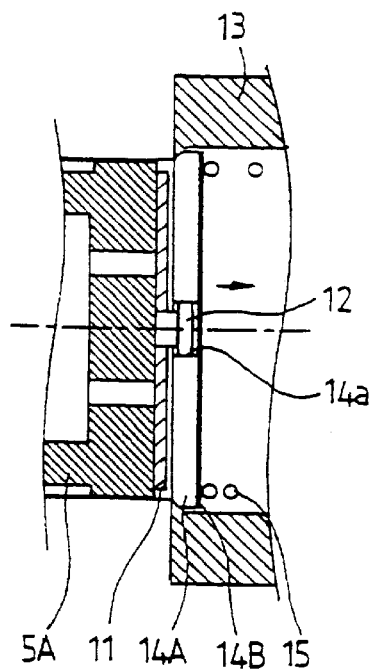
FIG. 6 is a cross-sectional view showing the axial flow valve system of FIG. 5 during the compression cycle.
Figure 7:
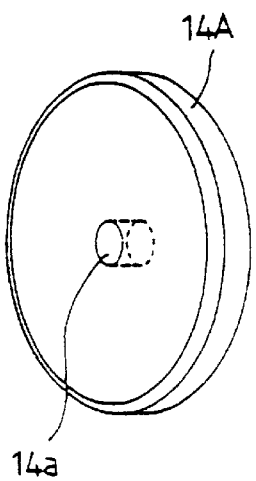
FIG. 7 is a perspective view showing a first exhaust valve of the axial flow valve system of FIG. 5 during the compression cycle.
Figure 8:
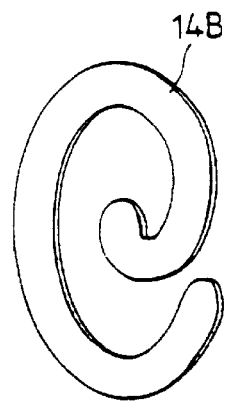
FIG. 8 is a perspective view showing a second exhaust valve of the axial flow valve system of FIG. 5 during the compression operation.
Figure 9:
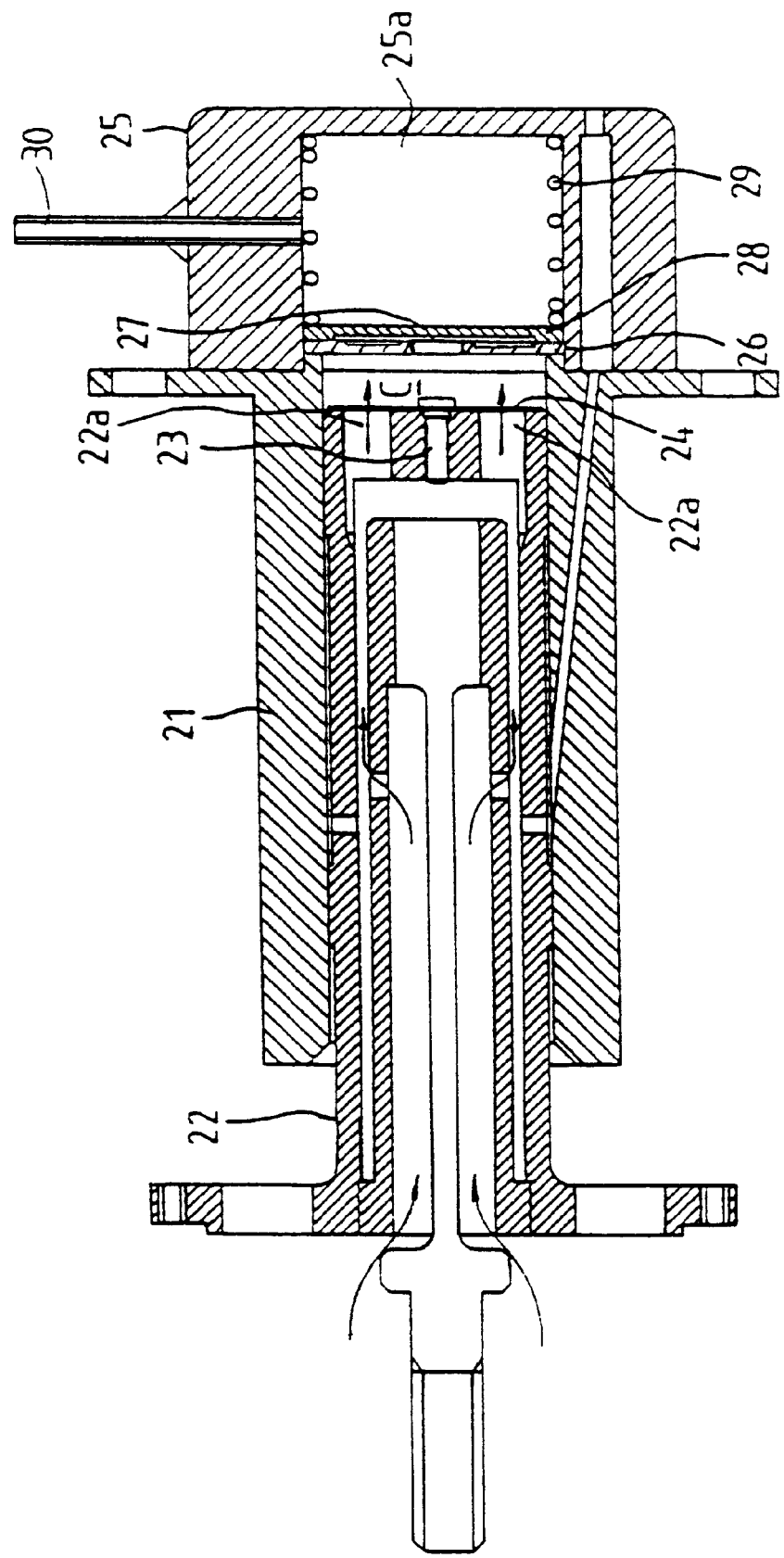
FIG. 9 is a cross-sectional view showing an axial flow valve system for a linear compressor according to a first embodiment of the present invention.

First, as shown in FIG. 9, in an axial flow valve system for a linear compressor according to a first embodiment of the present invention, an intake valve 24 is closely affixed without rocking on the central portion of a front end of a piston 22 disposed inside a cylinder 21 by a piston pin 23 for the purpose of passing a refrigerant therethrough.

First and second exhaust valves 26,27 are provided in an inner bore 25*a* of a head cover 25 fixed to one end of the cylinder 21.

At the rear side(the side opposite to the piston 22) of the second exhaust valve 27, a stopper 28 is disposed to prevent the second exhaust valve 27 from being pushed rearward, and between one end of the bore 25*a* of the head cover 25 and the stopper 28, a resilient member 29 such as a compression spring is disposed to resiliently support the first exhaust valve 26, the second exhaust valve 27 and the stopper 28.

Figure 10:
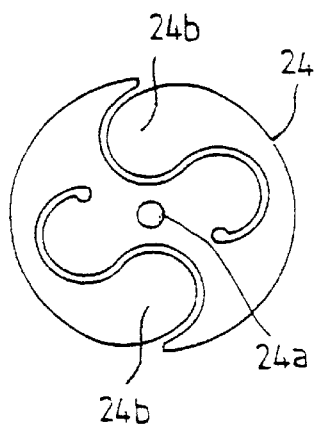
FIG. 10 is a front view of an intake valve adopted to an axial flow valve system for a linear compressor according to the first embodiment of the present invention.

The circular intake valve 24 in the axial flow valve system for a linear compressor according to the first embodiment of the present invention, as shown in FIG. 10, has a fixing hole 24*a* disposed at its central portion, and at its peripheral portion, has an intake opening-closing portions 24*b*,24*b* for resiliently opening and closing piston ports (not illustrated) disposed in the front portion of the piston 22.

Figure 11A:
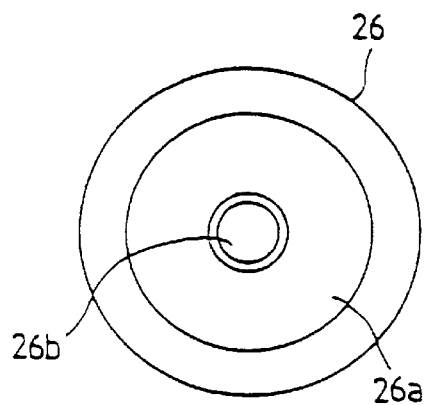
FIG. 11A is a rear view of a first exhaust valve adopted to an axial flow valve system for a linear compressor according to the first embodiment of the present invention.
Figure 11B:
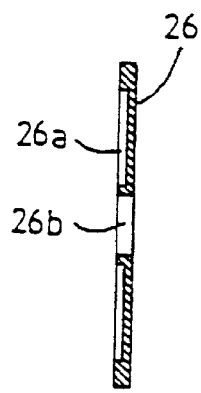
FIG. 11B is a cross-sectional view of a first exhaust valve adopted to an axial flow valve system for a linear compressor according to a first embodiment of the present invention.

The first exhaust valve 26, as shown in FIGS. 11A and 11B, has an annular recess 26*a* in its front side, and a first refrigerant exhaust port 26*b* at its central portion.

Figure 12:
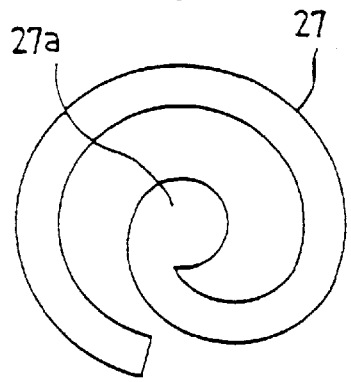
FIG. 12 is a front view of a second exhaust valve adopted to an axial flow valve system for a linear compressor according to the first embodiment of the present invention.

The second exhaust valve 27 is formed in a spiral shape, as shown in FIG. 12, and has formed at its central portion an exhaust opening-closing portion 27*a* for opening and closing the first refrigerant exhaust port 26*a* of the first exhaust valve 26.

Figure 13A:
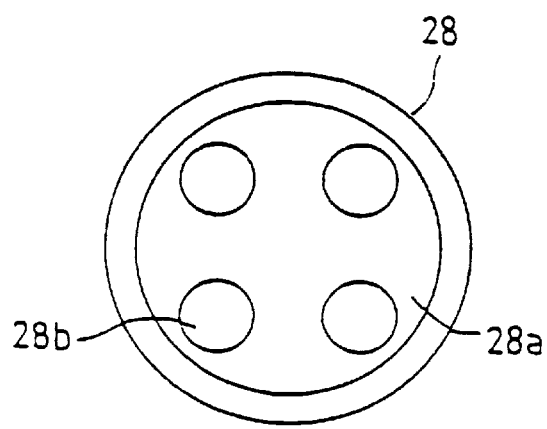
FIG. 13A is a front view of a stopper adopted to an axial flow valve system for a linear compressor according to the first embodiment of the present invention.
Figure 13B:
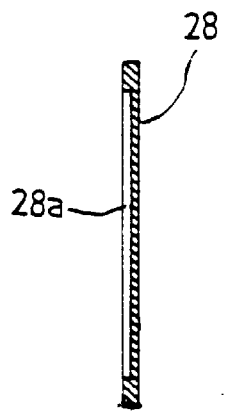
FIG. 13B is a cross-sectional view of the stopper.

In the front side of the stopper, as shown in FIGS. 13A and 13B, a circular recess 28*a* having a depth of 0.4~0.5 mm depth is formed, and a plurality of a second refrigerant exhaust port 28*b* are disposed at portions thereof where they are not contacted with the exhaust opening-closing portion of the second exhaust valve 27.

Reference numeral 30 denotes a refrigerant exhaust pipe.

The operation and effect of the axial flow valve system according to the first embodiment of the present invention will be described.

During the intake stroke of the piston, refrigerant supplied from the rear of the piston 22 proceeds in the direction of the arrow in FIG. 9, and passes through the ports of the piston 22, pushes open the intake opening-closing portions 24*b*,24*b* of the intake valve 24, and finally is sucked into the compression chamber (C).

Then, when the piston 22 is moved toward the first exhaust valve 26 and the compression cycle is performed, the refrigerant is compressed inside the compression chamber (C).

Here, during the compression stroke of the piston since the intake valve 24 is closely contacted with the front surface of the piston 22 and as a result closes the piston ports of the piston.

Then, the refrigerant compressed in the compression chamber (C) passes through the refrigerant exhaust port 26*b* of the first exhaust valve 26, pushes open the exhaust opening-closing portion 27*a* of the second exhaust valve 27, and then is discharged through the second refrigerant exhaust port 28*b* of the stopper 28 to the bore 25*a* of the head cover 25, and finally is discharged to the outside through the refrigerant exhaust pipe 30.

Here, since opening of the exhaust opening-closing portion 27*a* of the second exhaust valve 27 is limited by the stopper 28, the opening movement is not so large.

When the front end of the piston 22 contacts with the first exhaust valve 26, since the intake valve 24 fixed on the front surface of the piston 22 contacts the first exhaust valve 26, the force on the first exhaust valve 26, the second exhaust valve 27 and the stopper 28 exceeds the resilience of the resilient member 29 causing these elements to move rearwardly.

Thus, by the buffer action of the first exhaust valve 26, the valve is securely operated.

Here, the head portion of the piston pin 23 is inserted into the first refrigerant exhaust port 26*b* of the first exhaust valve 26, and thereby the intake valve 24 pushes against the first exhaust valve 26.

When the piston 22 is retracted once against to perform the intake cycle, the first refrigerant exhaust port 26*b* of the first exhaust valve is closed by the restoring force of the exhaust opening-closing portion 27*a* of the second exhaust valve 27 to prevent the further exhausting of the refrigerant, and the refrigerant supplied from the rear portion of the piston 22 passes through the piston ports in the piston 22, pushes open the intake opening-closing portions 24*b*,24*b* of the intake valve 24, and then is sucked into the compression chamber (C).

As described above, in accordance with the repeated linear reciprocating movement of the piston 22, the intake, compression and exhaust cycles of the refrigerant are performed.

Now, the axial flow valve system for a linear compressor according to a second embodiment will be described with reference to the accompanying drawings.

For the second through the seventh embodiments, only the construction and character of the fixed intake valve will be described.

Figure 14A:
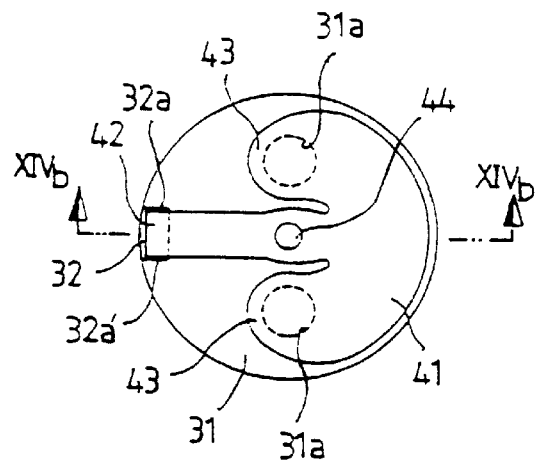
FIG. 14A is a front view of a piston to which an intake valve is fixed as adopted in an axial flow valve system for a linear compressor according to second embodiment of the present invention.
Figure 14B:
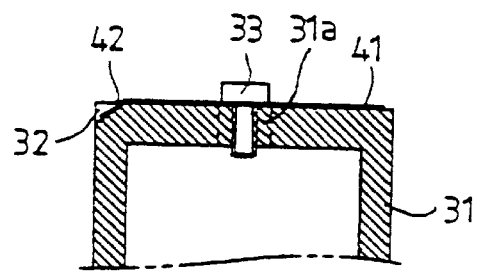
FIG. 14B is a cross-sectional view taken along the line XIV*b*—XIV*b* in FIG. 14A.

As shown in FIGS. 14A and 14B, in an axial flow valve system for a linear compressor according to second embodiment, a notch 32 having a wall 32a,32a' at each side is formed to have 0.1~0.5 mm depth in the outer front circumferential portion of the piston 31. To the front central portion of the piston 31 an intake valve 41 fixed with a piston pin 33 having a locating portion 42 inserted in the notch 32 in the piston 31.

The intake valve 41 also has the intake opening-closing portions 43,43 symmetrically disposed for opening and closing the piston ports 31a,31a provided at the front portion of the piston 31. In the center of the intake valve 41, there is formed a fixing hole 44 for fixing a piston pin 33 and the locating portion 42 extends between the intake opening-closing portions 43,43 in the radial direction.

In the axial flow valve system for a linear compressor according to the second embodiment having the above-described construction, since the notch 32 with the walls 32a,32a' is formed at the front portion of the piston 31 and the intake valve 41 includes the extended locating portion 42, when the intake valve 41 is fixed to the piston 31 by the piston pin 33, the end of the locating portion 42 is held between the walls 32a,32a' of the notch 32 in the piston 31, and consequently the intake valve 41 can be fixed in a more stable position.

In addition, during the operation of the intake valve 41, the arbitrary movement or rotation of the intake valve 41 is prevented, resulting in the improved reliability in the opening and closing of the intake valve 41.

Figure 15:
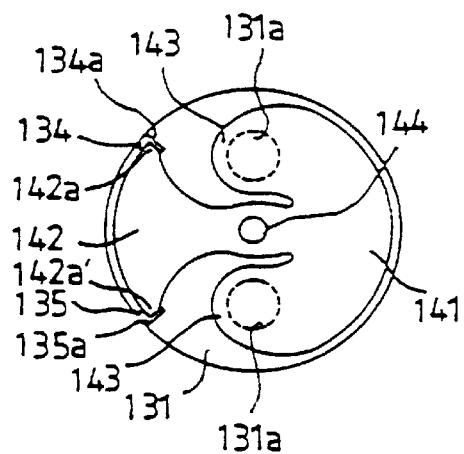
FIG. 15 is a front view of an axial flow valve system for a linear compressor according to a third embodiment of the present invention.

As shown in FIG. 15, in the axial flow valve system for a linear compressor according to the third embodiment of the present invention, a locating portion 142 is formed similarly to portion 42 in FIG. 14 but made wider, and latching portions 142a,142a' are formed at the edges thereof and notches 134,135 are formed having walls 134a,135a at both sides of the front outer circumferential portion of the piston 131.

Therefore, due to the large width of the locating member 142, the strength of the intake valve 141 is advantageously reinforced.

Figure 16A:
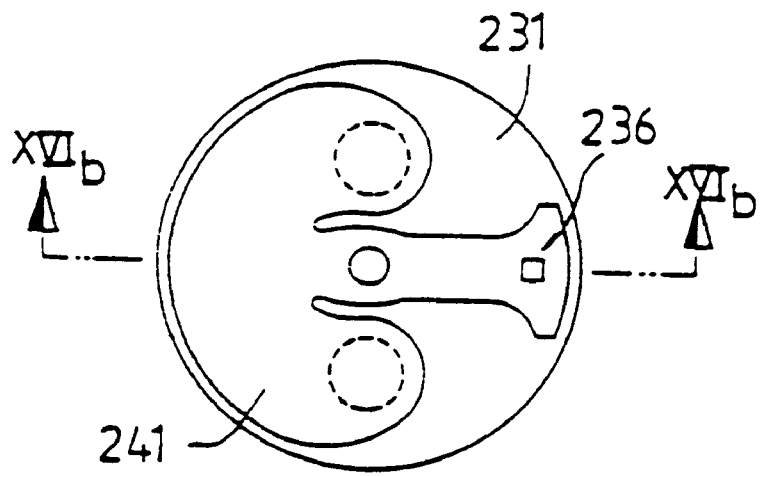
FIG. 16A is a front view of an axial flow valve system for a linear compressor according to a fourth embodiment of the present invention.
Figure 16B:
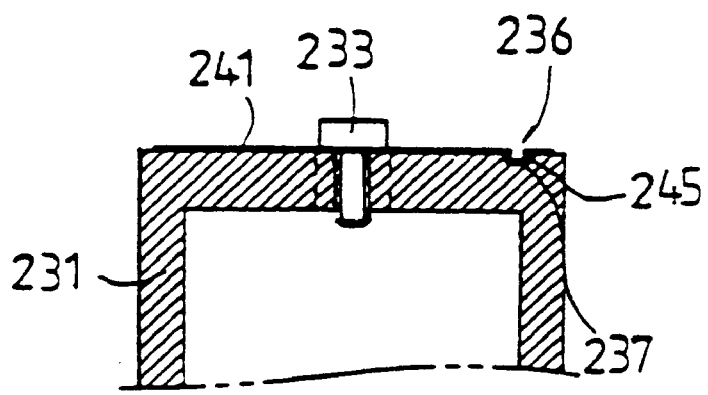
FIG. 16B is a cross-sectional view taken along the line XIV*lb*—XIV*lb* in FIG. 16A.

As shown in FIGS. 16A and 16B, in the axial flow valve system for a linear compressor according to the fourth embodiment of the present invention, the intake valve 241 is located to the piston 231 by means of a square projection 236, and the intake valve 241 is fixed to the piston 31 with the piston pin 233.

The square projection 236 formed on the extended locating portion of the intake valve 241 is received in a square recess 237 formed in a front portion of the piston 231.

In the above-described fourth embodiment of the present invention, since the piston 231 and the intake valve 241 are closely combined with each other and the intake valve 241 is fixed to the piston 231 by the piston pin 233, as a result the intake valve 241 can be fixed to the piston 231 more firmly and precisely.

Here, the portions for forming the projection 236 and the recess 237 are not limited to the embodiment shown in the drawing, and it may be possible that the recess 237 is formed on the piston 231 and the projection 237 is formed in the intake valve 241.

It is preferable that if the projection 236 formed on the intake valve 241 and the square recess 237 is formed in the piston 231 that these elements be formed at a portion in which the movement of the intake valve 241 does not occur and the number of the elements 236,237 is not limitative.

Figure 17A:
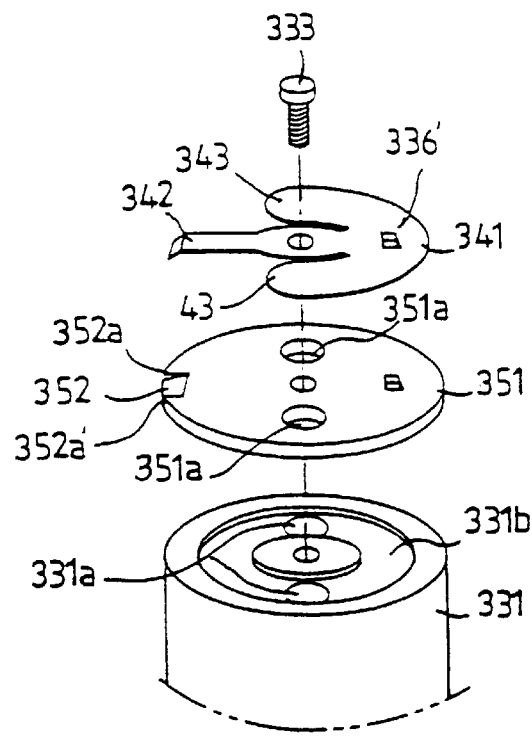
FIG. 17A is an exploded perspective view showing an axial flow valve system for a linear compressor according to a fifth embodiment of the present invention.
Figure 17B:
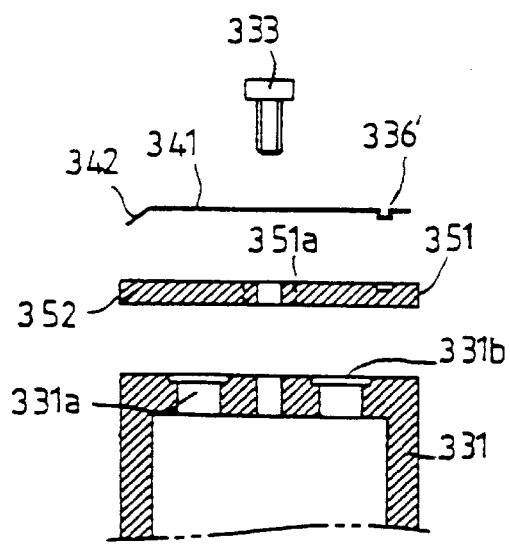
FIG. 17B is an exploded cross-sectional view showing the axial flow valve system for a linear compressor according to the fifth embodiment of the present invention.

As shown in FIGS. 17A and 17B, in an axial flow valve system for a linear compressor according to the fifth embodiment of the present invention, between a piston 331 and an intake valve 341 there is provided an intervalve 351 communicated with piston ports 331a of the piston 331 and opened and closed by intake opening and closing portions 343.

The intervalve 351 is in the shape of a circular disk having a predetermined thickness, and is fixed by inserting a piston pin 333 through a hole in its center, at the sides of which are formed two valve holes 351a,351a.

Here, the intervalve 351 is fabricated through a simple sintering, eliminating the need for hardening of the surface of the piston 331.

The intake valve 341 is fixedly attached to the intervalve 351 and the piston 331 by adopting the fixed intake valve structure shown in FIGS. 14 and 16.

That is, in a portion of the front outer circumferential portion of the intervalve 351, a notch 352 is formed having walls 352a,352a' at both sides with a predetermined depth. A portion of the intake valve 341 is extended to form a locating portion 342 which is inserted in the notch 332 in the intervalve or the intake valve is fixed by a square projection 336' mating with a square recess 337 in the intervalve 351.

Here, a circular recess having a predetermined depth is formed in a front surface of piston 331 on which the piston ports 331a are disposed for the in-flowing of a refrigerant.

As shown in FIGS. 17A and 17B, by adopting the fixed intake valve structure shown both in FIGS. 14 and 16 to the intervalve 351 and the intake valve 341, the reliability of the intake valve 341 can be enhanced.

Figure 18:
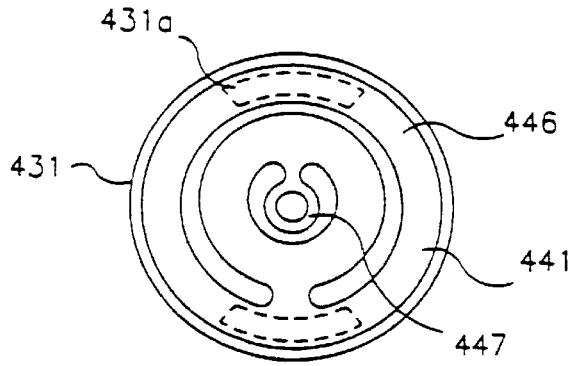
FIG. 18 is a front view of an axial flow valve system for a linear compressor according to a sixth embodiment of the present invention.

As shown in FIG. 18, in an axial flow valve system for a linear compressor according to the sixth embodiment of the present invention, a circular hub 447 is formed for fastening the piston pin(not illustrated) to fix the intake valve 441, and at an outer circumferential portion of the circular hub 447 is provided an annular opening-closing portion for opening and closing piston ports 431a,431a of the piston 431.

Here, the circular hub 447 and the annular opening-closing portion are connected with each other, respectively.

Therefore, when the intake valve 441 is fixed to the piston by piston pin, although the position of the intake valve 441 is not fixed, since the opening-closing portion 446 blocks the piston ports 431a,431a of the piston 431 all the time, the function of the intake valve 441 can be properly carried out.

Figure 19A:
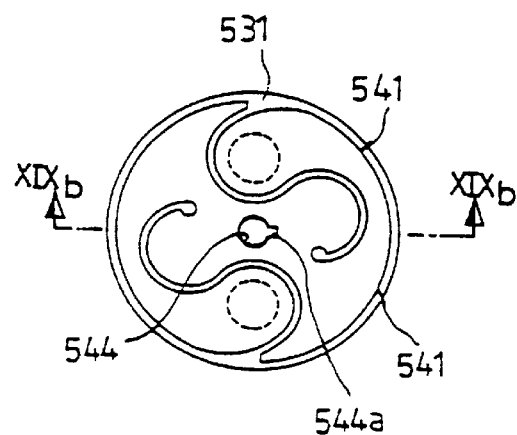
FIG. 19A is a front view showing an axial flow valve system for a linear compressor according to a seventh embodiment of the present invention.
Figure 19B:
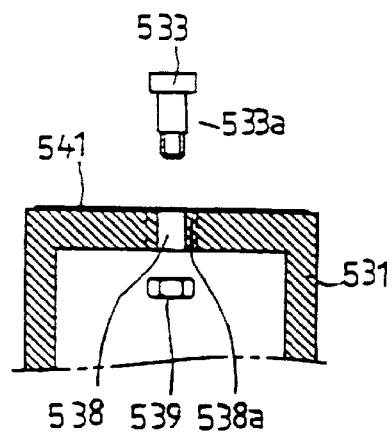
FIG. 19B is an exploded cross-sectional view taken along the line XIX*b*—XIX*b* in FIG. 19A.

As shown in FIG. 19, in an axial flow valve system for a linear compressor according to the seventh embodiment of the present invention, the shape of the intake valve according to the first embodiment of the present invention is applied to the shape of an intake valve 541, wherein a key groove 544a is formed in a fixing hole 544, and a key 538a is formed in a pin hole 538 fixed at a central portion of a front surface of a piston 531.

And, by forming the key groove 538a in the intake valve 541 and the key 533a on the piston pin 533 for fixing the intake valve 541, when the piston pin 533 is fixed in the pin hole 538 of the piston 531 with the intake valve 541 affixed, a nut 539 is locked on the end portion of the piston pin 533 protruded into the piston 531 or the piston pin 533 is fixed by means of caulking.

That is, in the axial flow valve system for a linear compressor according to the seventh embodiment of the present invention, the intake valve can be fixed more firmly in the correct position as follows.

After aligning the key groove 538a disposed in the pin hole 538 of the piston 531 with the key groove 544a provided in the fixing hole 544 of the intake valve 541, the piston pin 533 on which the key 533a is formed is inserted, and then the nut is fastened to the end of the piston pin 533 protruded into the piston 531 or the caulking is performed.

As described above in detail, the axial flow valve system for a linear compressor according to the present invention has a double exhaust valve construction including the first exhaust valve and the second exhaust valve, and by disposing the stopper at the back of the second exhaust valve, a more prompt and reliable opening and closing of the exhaust valve can be obtained.

In addition, the efficiency of the linear compressor can be enhanced by preventing the intake valve from moving axially, by preventing the intake valve from sticking to the front surface of the piston due to the oil used for lubrication of the piston, and by preventing the friction between the intake valve and the piston pin.

Further, by fixing the intake valve in a proper position on the front surface of the piston and thereby securing the reliability of the intake valve, the efficiency of the linear compressor can also be enhanced.

Although the preferred embodiments of the present invention have been disclosed for illustrative purposes, those skilled in the art will appreciate that various modifications, additions and substitutions are possible, without departing from the scope and spirit of the invention as recited in the accompanying claims.

We claim:

1. An axial flow valve system for a linear compressor, comprising:

an intake valve closely fixed without rocking on a central portion of a front end of a piston disposed inside a cylinder by a piston pin for passing a refrigerant;

an exhaust valve and an exhaust valve closing member provided in an inner bore of a head cover fixed to one end of the cylinder;

a resilient member disposed at one side of the inner bore of the head cover for resiliently supporting the exhaust valve and the exhaust valve closing member; and a stopper provided between the exhaust valve closing member and the resilient member for preventing the exhaust valve closing member from being pushed rearwardly until the resiliency of the resilient member is exceeded.

2. The valve system of claim 1, wherein the stopper has an annular recess having a predetermined depth formed on its front surface; and a plurality of refrigerant exhaust ports disposed therein at a portion thereof in which they are not contacted with a discharging opening-closing portion of the second exhaust valve.

3. The valve system of claim 1, wherein a notch is formed at a front outer circumferential portion of the piston, and a locating portion is formed on the intake valve to be inserted in the notch in the piston.

4. The valve system of claim 1, wherein the piston and the intake valve are located relative to one another by means of at least one recess formed therein and one projection formed thereon, respectively.

5. The valve system of claim 1, wherein in the intake valve, a circular hub is formed for fastening a piston pin therethrough and at an outer circumferential portion of the circular hub is provided an annular opening-closing portion for opening and closing piston ports in the piston.

6. The valve system of claim 1, wherein a key groove is formed in a pin hole of the piston, and another key groove is formed in a fixing hole of the intake valve and wherein the piston pin is provided with a key.

7. An axial flow valve system for a linear compressor, comprising:

a piston disposed inside a cylinder and having a recessed front end;

an intervalve closely combined at a central portion of the front end of the piston;

an intake valve contacted with the intervalve and fixed to the piston without rocking to pass a refrigerant, having a fixing hole at a center thereof for being fastened by a piston pin, and at its peripheral portion having a resilient member for opening and closing a piston port disposed in a front portion of the piston;

the resilient member disposed at one side of an inner bore, a head cover for resiliently supporting an exhaust valve, an exhaust valve closing member and a stopper; and the stopper provided between the exhaust valve closing member and the resilient member for preventing the exhaust valve closing member from being pushed rearwardly until the resiliency of the resilient member is exceeded.

8. The valve system of claim 7, wherein the intervalve has a valve hole opened and closed by the intake valve and communicating with the piston ports of the piston.

9. The valve system of claim 8, wherein a notch is formed at a front outer circumferential portion of the intervalve and a locating portion of the intake valve is extended to be inserted in the notch in the intervalve.

10. The valve system of claim 8, wherein the intervalve and the intake valve are located relative to one another by means of at least one recess formed therein and one projection formed thereon, respectively.

* * * * *